United States Patent [19]
Currie et al.

[11] Patent Number: 5,366,454
[45] Date of Patent: Nov. 22, 1994

[54] IMPLANTABLE MEDICATION DISPENSING DEVICE

[75] Inventors: John F. Currie, Montreal; Dentcho V. Ivanov, Pierrefonds; Andre Lecours, Longueuil, all of Canada

[73] Assignee: La Corporation de l'Ecole Polytechnique, Montreal, Canada

[21] Appl. No.: 32,991

[22] Filed: Mar. 17, 1993

[51] Int. Cl.$^5$ ............... A61K 9/11; A61M 37/00; B65D 47/10
[52] U.S. Cl. .................. 604/890.1; 604/891.1; 604/66; 604/88; 604/244; 604/246; 137/68.1; 222/541
[58] Field of Search .......... 604/22, 244, 246, 88, 604/82, 153, 890.1–891.1; 607/97; 128/24 AA; 137/68.1; 222/541

[56] References Cited

U.S. PATENT DOCUMENTS

| | | | |
|---|---|---|---|
| 3,692,027 | 9/1972 | Ellinwood, Jr. | 604/891.1 |
| 4,870,953 | 10/1989 | DonMichael et al. | 128/24 AA |
| 4,936,281 | 6/1990 | Stasz | 128/660.03 |
| 5,059,175 | 10/1991 | Hanover et al. | 604/890.1 |
| 5,102,402 | 4/1992 | Dror et al. | 604/265 |
| 5,156,591 | 10/1992 | Gross et al. | 607/153 |

FOREIGN PATENT DOCUMENTS 8600519  1/1986  WIPO ............ 604/890.1

OTHER PUBLICATIONS

W. P. Robbins et al., "Linear Motion Microactuators Using Piezoelectric Thin Films", Proc. Int. Conf. Solid-State Sensors and Actuators (Transducers '91), San Francisco, Calif., Jun. 1991, pp. 55-58.

*Primary Examiner*—C. Fred Rosenbaum
*Assistant Examiner*—Mark Bockelman
*Attorney, Agent, or Firm*—Swabey Ogilvy Renault

[57] ABSTRACT

A medication dispensing device for implantation into an animal or human body, comprises a plurality of compartments each containing a dose of medicine to be dispensed and having a delivery opening permitting delivery of the medicine; a rupturable membrane sealing the delivery opening of each compartment, the membrane having a predetermined elastic deformation limit and a predetermined rupture point; and a membrane rupturing system associated with each compartment for rupturing the membrane thereof in response to an electrical signal. The membrane rupturing system includes a stress-inducing member maintaining the membrane stressed to substantially the elastic deformation limit thereof, and a piezoelectric transducer responsive to the electrical signal for applying to the membrane additional stress sufficient to exceed the rupture point of the membrane, thereby causing the membrane to rupture and allowing body fluids to enter into the compartment for mixing with the medicine contained therein so that the medicine is released in admixture with the body fluids through the delivery opening into the animal or human body. The medication dispensing device of the invention further comprises a control circuit connected to a power source for supplying the electrical signal to a respective piezoelectric transducer of each membrane rupturing system to activate the respective piezoelectric transducer.

25 Claims, 3 Drawing Sheets

IMPLANTABLE MEDICATION DISPENSING DEVICE

BACKGROUND OF THE INVENTION

The present invention relates to an implantable medication dispensing device. More particularly, the invention is directed to a device for implantation into an animal or human for delivery of medicine to the animal or human at specific intervals over a long period of time.

Various implantable drug dispensers are known in the art. For example, U.S. Pat. No. 3,692,027 discloses an implantable, timed drug dispenser that dispenses the drug mechanically. The dispenser comprises a case and a circular medication storage wheel member which is rotatably mounted within the case, the wheel member having an outer peripheral face with a plurality of cavities formed therein. Each cavity contains a capsule of the desired medication and has an associated piston member which when moved radially outward in a timed sequence ejects its respective capsule through an aperture formed in the case. The wheel member driven by a battery powered clock mechanism. Since many moving parts are involved in the drug delivery, such a mechanical dispenser is generally sensitive to shock and therefore is not reliable.

U.S. Pat. No. 5,059,175, on the other hand, discloses an implantable drug dispenser which is electrically operated to actuate a plunger for dispensing the drug. The dispenser comprises a tubular housing having a plurality of elongated, drug containing vesicles formed therein. Disposed in each vesicle near the bottom thereof is a plunger adapted to be forced upwardly in the vesicle by gas pressure. The housing includes a bottom compartment in which is disposed a plurality of pyrotechnic gas generating beads each associated with a respective vesicle and responsive to heat resulting from an electrical signal applied to a heating element, thereby igniting and producing gas which forces a corresponding plunger upwardly in the respective vesicle. The plunger in turn forces the drug contained in the vesicle against a rupturable cover to rupture the cover and thereby push the drug out of the vesicle. Such a drug dispenser requires gas-tight vesicles and these are often prone to leakage. In addition, the ignition of the pyrotechnic gas generating beads produces heat as well as hot and high pressure gases that may induce high levels of stress, which in turn may lead to material breakage and an uncontrolled release of drug.

SUMMARY OF THE INVENTION

It is therefore an object of the invention to overcome the above drawbacks and to provide an implantable medication dispensing device which is capable of repeatedly delivering doses of medicine in a reliable manner and which does not necessitate an ejection mechanism for delivering the medicine.

In accordance with the present invention, there is provided a medication dispensing device for implantation into an animal or human body, comprising a plurality of compartments each containing a dose of medicine to be dispensed and having a delivery opening permitting delivery of the medicine; a rupturable membrane sealing the delivery opening of each compartment, the membrane having a predetermined elastic deformation limit and a predetermined rupture point; and a membrane rupturing system associated with each compartment for rupturing the membrane thereof in response to an electrical signal. The membrane rupturing system includes stress-inducing means maintaining the membrane stressed to substantially the elastic deformation limit thereof, and piezoelectric transducer means responsive to the electrical signal for applying to the membrane additional stress sufficient to exceed the rupture point of the membrane, thereby causing the membrane to rupture and allowing body fluids to enter into the compartment for mixing with the medicine contained therein so that the medicine is released in admixture with the body fluids through the delivery opening into the animal or human body. The medication dispensing device of the invention further comprises means for supplying the electrical signal to a respective piezoelectric transducer means of each membrane rupturing system to activate the respective piezoelectric transducer means.

Certain classes of materials exhibit what is called the piezoelectric effect: the generation of electric polarization in the material as a result of the application of mechanical stress. The reverse effect is also found, in which application of a voltage between certain faces of the material produces a mechanical distortion of the material. Applicant has found quite unexpectedly that the reverse piezoelectric effect can be used to rupture a membrane which retains a medicine captive in a medicine-containing compartment, provided that the membrane is maintained under a stressed condition by adjusting the stress in the membrane to substantially the elastic deformation limit thereof. Examples of suitable piezoelectric materials which can be used in the present invention are lead zirconate titanate, zinc oxide and cadmium sulphide.

In a preferred embodiment of the invention, the device has a wafer-like body with a plurality of spaced-apart cavities formed therein, each cavity defining a respective one of the aforesaid compartments. The membrane of each compartment can be either integral with the wafer-like body or bonded thereto. Preferably, the cavities each extend through the wafer-like body to define a charging opening opposite the delivery opening for charging each compartment with medicine, and a closure member is bonded to the wafer-like body for sealing the charging openings.

According to another preferred embodiment, at least one of the aforesaid compartments has at least one associated secondary compartment containing a dose of another medicine to be mixed with the medicine contained in the one compartment, the secondary compartment being separated from the one compartment by a partition comprising a further rupturable membrane. A further membrane rupturing system is associated with the secondary compartment for rupturing the further membrane thereof in response to a further electrical signal. The electrical signal supplying means is operative to sequentially apply the further electrical signal to the further membrane rupturing system and the aforesaid electrical signal to the membrane rupturing system of the one compartment, so as to first cause rupture of the further membrane and mixing of the medicine with the other medicine, and then cause rupture of the membrane of the one compartment for release of the mixed medicines into the animal or human body.

In a particularly preferred embodiment of the invention, the membrane rupturing system comprises two assemblies of the aforesaid stress-inducing means and piezoelectric transducer means, the assemblies being arranged in spaced-apart opposed relationship on the membrane of each compartment. The stress-inducing means of each assembly comprises a stress-inducing thin film on the membrane whereas the piezoelectric transducer means comprises two electrically conductive thin films and a piezoelectric thin film disposed therebetween, one of the electrically conductive thin films being arranged between the stress-inducing thin film and the piezoelectric thin film. The piezoelectric transducer means of the assemblies coact to apply to the membrane the aforesaid additional stress and thereby cause the membrane to rupture between the assemblies.

The expression "thin film" as used herein means a film having a thickness ranging from about 0.05 to about 1 $\mu$.

Preferably, the piezoelectric transducer means of one assembly is operative to deform a portion of the membrane in a first direction and the piezoelectric transducer means of the other assembly is operative to deform an adjacent portion of the membrane in a second direction opposite the first direction, so as to apply the aforesaid additional stress to the membrane. To this end, the one electrically conductive thin film defines a ground electrode and the other electrically conductive thin film defines a voltage electrode, and the electrical signal applied to the piezoelectric transducer means is such that the voltage electrode of one assembly is positive with respect to the ground electrode thereof and the voltage electrode of the other assembly is negative with respect to the ground electrode thereof.

Where the stress-inducing thin film is electrically conductive, or slightly electrically conductive such as in the case of a thin film of polysilicon, an electrically insulating thin film is disposed between the stress-inducing thin film and the aforesaid one electrically conductive thin film of each assembly.

The medication dispensing device of the invention advantageously includes detector means associated with each compartment for detecting rupture of the membrane thereof. Preferably, a common electrically insulating thin film is disposed between the stress-inducing thin film and the one electrically conductive thin film of each assembly, the common electrically insulating thin film extending on the membrane between the assemblies over a membrane rupturing zone. The detector means comprises an electrically conductive thin film strip disposed on the common electrically insulating thin film and forming an electrical path across the membrane rupturing zone, and a monitoring circuit connected to the electrically conductive thin film strip for detecting passage of electrical current therethrough, a further electrically insulating thin film being disposed between the electrically conductive thin film strip and the one electrically conductive thin film of each assembly. Rupture of the membrane causes rupture of the common electrically insulating thin film and of the electrically conductive thin film strip thereon so that rupture of the membrane is detected by the monitoring circuit as an open circuit.

According to another preferred embodiment of the invention, the stress-inducing means comprises a stress-inducing thin film disposed on the membrane of each compartment and extending substantially completely over the delivery opening thereof. The piezoelectric transducer means, on the other hand, comprises first and second electrically conductive thin films defining respectively first and second voltage electrodes, a third electrically conductive thin film defining a ground electrode and a piezoelectrical thin film disposed between the ground electrode and the first and second voltage electrodes, the ground electrode being arranged between the stress-inducing thin film and the piezoelectric thin film. The first and second voltage electrodes are each patterned to form a plurality of elongated electrode elements arranged in spaced-apart parallel relationship across the delivery opening with the electrode elements of the first voltage electrode extending between the electrode elements of the second voltage electrode. The first and second voltage electrodes, the ground electrode and the piezoelectric thin film cooperate together to apply to the membrane the aforesaid additional stress and thereby cause the membrane to rupture, rupture of the membrane leading to rupture of the stress-inducing thin film, the first, second and third electrically conductive thin films and the piezoelectric thin film.

Preferably, the first and second voltage electrodes and the ground electrode cooperate with the piezoelectric thin film to deform portions of the membrane in a common direction so as to apply the aforesaid additional stress to the membrane. To this end, the electrical signal applied to the piezoelectric transducer means is such that the first voltage electrode is positive with respect to the ground electrode and the second voltage electrode is negative with respect to the ground electrode.

A detector means is also advantageously associated with each compartment for detecting rupture of the membrane, the stress-inducing thin film, the first, second and third electrically conductive thin films and the piezoelectric thin film. Such a detector means preferably comprises a monitoring circuit connected to a respective one of the first and second voltage electrodes for detecting passage of electrical current through the respective voltage electrode, rupture of the membrane, the stress-inducing thin film, the first, second and third electrically conductive thin films and the piezoelectric thin film being detected by the monitoring circuit as an open circuit.

The electrical signal supplying means used according to the invention preferably comprises a power source and a time-controlled switching circuit for temporarily coupling the power source to the respective piezoelectric transducer means at a predetermined time. The power source is advantageously a rechargeable electrochemical cell that can be recharged by an integrated solid state charging means such as a photodiode which produces power from low-intensity .Light transmitted through the skin of the animal or human, a low-power magnetically coupled device or a low-power radio-frequency transmitter-receiver. The electrical signal supplying means can also incorporate means for receiving an externally transmitted command signal for initiating operation of the switching circuit, as well as multi-sensor means for activating the switching circuit upon detection of specific chemical or biological conditions, such as arterial pressure, pH, glucose concentration, insulin concentration, etc.

The medication dispensing device according to the invention can be used for delivering enzymes, hormones, neural stimulators, organic and inorganic salts directly into the blood stream or neural canals.

BRIEF DESCRIPTION OF THE DRAWINGS

Further features and advantages of the invention will become more readily apparent from the following description of preferred embodiments illustrated by way of examples in the accompanying drawings, in which.

DESCRIPTION OF PREFERRED EMBODIMENTS

Figure 1:
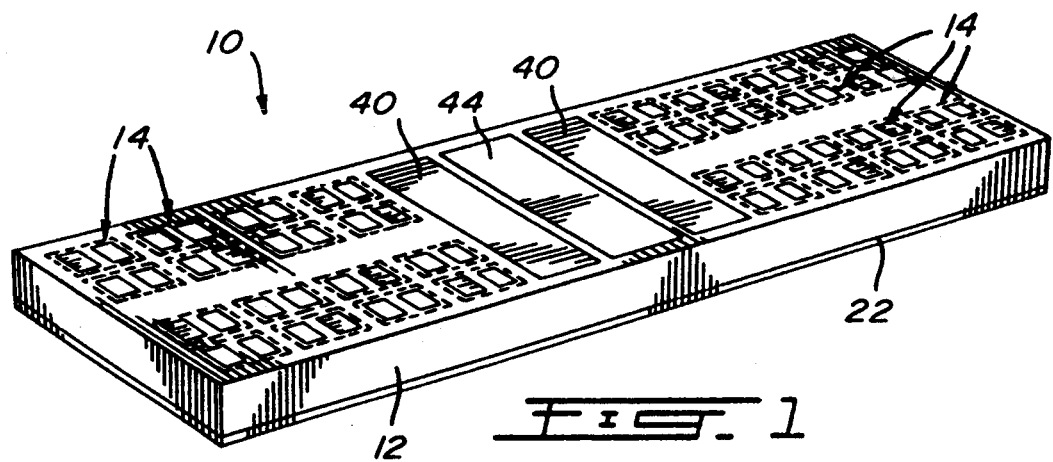
FIG. 1 is a perspective view of an implantable medication dispensing device according to a preferred embodiment of the invention.
Figure 2:
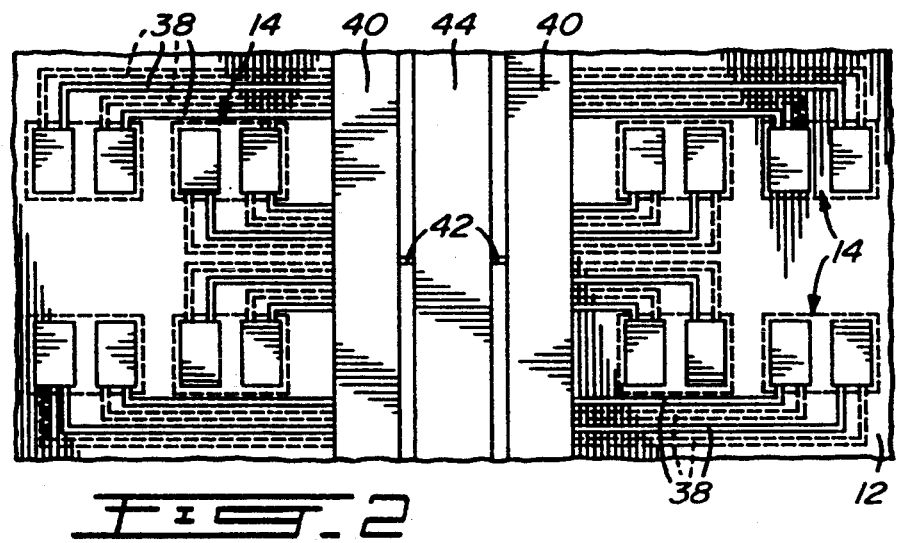
FIG. 2 is a fragmentary top plan view of the device shown in FIG. 1.
Figure 3:
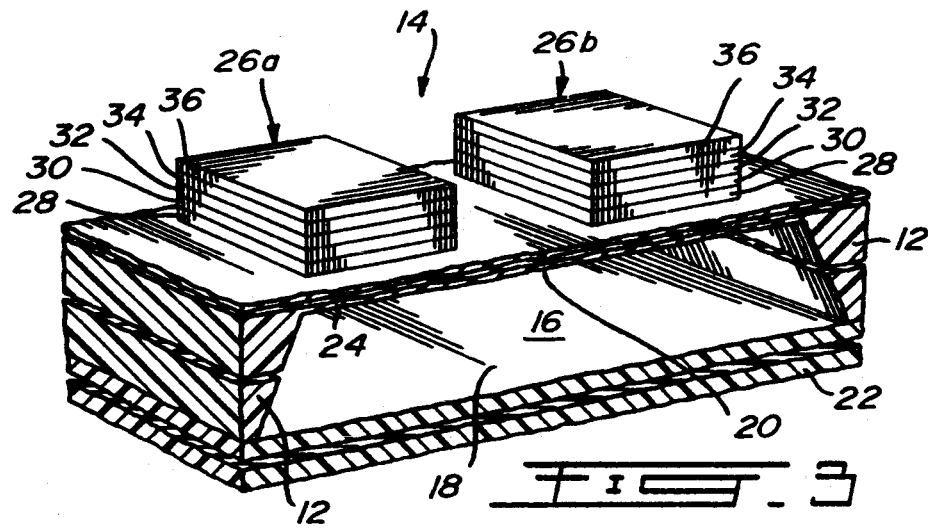
FIG. 3 is a fragmentary perspective view showing one of the medication delivery units of the device illustrated in FIG. 1.

Referring first to FIGS. 1-3, there is illustrated an implantable medication dispensing device 10 having a wafer-like silicon body 12 provided with a plurality of spaced-apart medication delivery units 14. Each unit 14 has a medicine-containing compartment 16 which is defined by a cavity formed in the body 12. The compartments 16 are each provided with a charging opening 18 for charging each compartment with the medicine to be dispensed, and with a delivery opening 20 permitting delivery of the medicine contained therein. A closure member 22 composed of silicon is anodically bonded to the body 12 for sealing the charging openings 18. The delivery openings 20, on the other hand, are sealed by a rupturable membrane 24 having a predetermined elastic deformation limit and a predetermined rupture point.

In the embodiment 14 illustrated in FIG. 3, the membrane 24 is integral with the body 12. Such a membrane, however, can be formed separately from the body and bonded thereto, such as in the case of the embodiment 14a illustrated in FIG. 4, in which a silicon membrane 24' is anodically bonded to the silicon body 12'.

A membrane rupturing system in the form of two assemblies 26a,26b of stacked thin films is associated with each medication delivery unit 14 for rupturing the membrane 24 in response to an electrical signal. The assemblies 26a and 26b are arranged in spaced-apart opposed relationship on the membrane 24. Each assembly comprises a stress-inducing thin film 28 deposited on the membrane 24, an electrically insulating thin film 30 deposited on the thin film 28, a first electrically conductive thin film 32 deposited on the thin film 30, a piezoelectric thin film 34 deposited on the thin film 32 and a second electrically conductive thin film 36 deposited on the thin film 34. Deposition of the thin films 28, 30, 32 and 36 can be effected by chemical vapor deposition, plasma chemical vapor deposition, e-beam evaporation or reactive sputtering techniques. The piezoelectric thin film 34 is a thin film of lead zirconate titanate; however, other piezoelectric materials such as zinc oxide and cadmium sulphide may be used. It is preferably deposited by reactive sputtering technique on the thin film 32.

Figure 9:
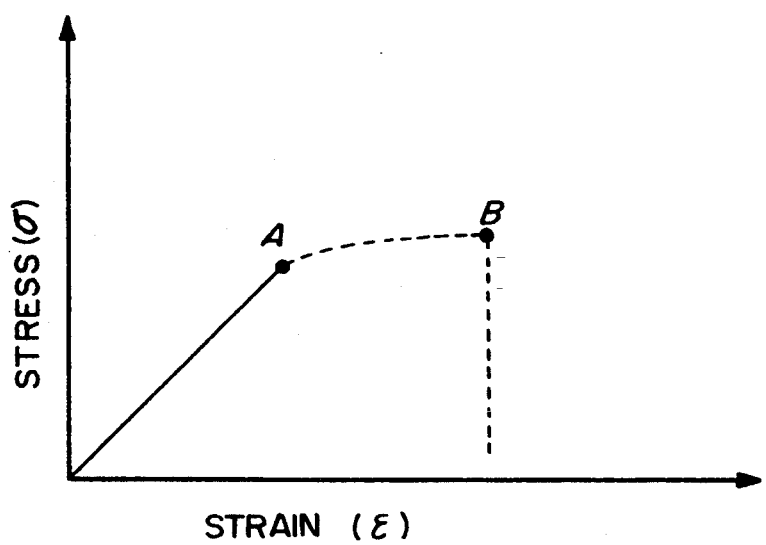
FIG. 9 is a graph showing the relationship between the strain and the stress in the membrane of a medication delivery unit according to the invention, leading to rupture of the membrane.

The stress-inducing thin film 28 is a thin film of polysilicon which is deposited on the silicon membrane 24 so as to maintain the membrane stressed to substantially the elastic deformation limit thereof, which elastic deformation limit is represented by point A in FIG. 9. The stress in the membrane 24 can reach $10^{11}$ Pa. The electrically conductive thin films 32 and 36 define ground and voltage electrodes, respectively. These electrodes are connected by thin film leads 38 to a time-controlled switching circuit 40 which in turn is connected by a thin film lead 42 to a rechargeable power source 44; the power source is a thin film electrochemical cell deposited on the body 12. The time-controlled switching circuit 40 is operative to temporarily couple the power source 44 to the respective electrodes 32,36 of assemblies 26a and 26b, at a predetermined time. As shown in FIGS. 1 and 2, the device 10 comprises two such circuits 40.

The piezoelectric thin film 34 together with the electrodes 32 and 36 define a transducer which is responsive to the electrical signal supplied by the switching circuit 40, for applying to the membrane 24 additional stress sufficient to exceed the rupture point of the membrane and thereby cause rupture thereof. Upon generation of an electric field between the electrodes 32 and 36, the piezoelectric thin film 34 either expands or contracts along its thickness depending on the voltage polarity of the electrode 36 with respect to the ground electrode 32. Thus, if the electrical signal applied by the switching circuit 40 is such that the voltage electrode 36 of assembly 26a is negative with respect to the ground electrode 32 thereof and the voltage electrode 36 of assembly 26b is positive with respect to the ground electrode 32 thereof, the deformation which the piezoelectric thin film 34 of assembly 26a undergoes, due to the reverse piezoelectric effect, will cause a corresponding deformation of a portion of the membrane in one direction (represented by arrow 46 in FIG. 4) and the deformation of the piezoelectric thin film 34 of assembly 26b will cause a corresponding deformation of an adjacent portion of the membrane in the opposite direction (represented by arrow 48 in FIG. 4), so that additional stress will be applied to the membrane 24. As shown in FIG. 9, since the membrane 24 is already maintained under a stress approaching the elastic deformation limit A, the additional stress applied by the transducer 32,34,36 of assemblies 26a,26b will cause the stress in the membrane 24 to exceed the rupture point B thereof, resulting in rupture of the membrane between the assemblies 26a and 26b. Once the membrane 24 has ruptured, body fluids of the animal or human in which the device 10 is implanted enter into the compartment 16 and mix with the medicine contained therein so that the medicine is released in admixture with the body fluids through the delivery opening 20 into the animal or human.

Figure 4:
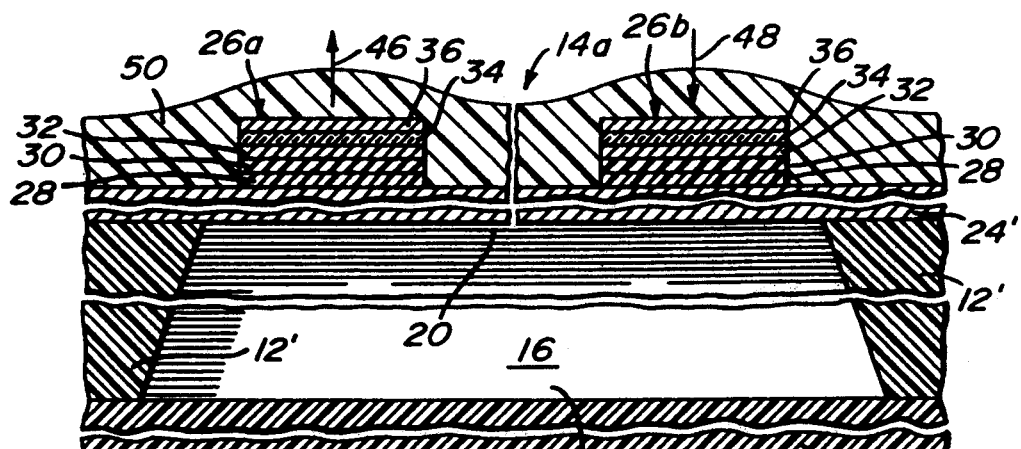
FIG. 4 is a fragmentary sectional view showing a medication delivery unit according to a further preferred embodiment of the invention.

As shown in FIG. 4, a bio-compatible polymeric film 50 encapsulates the dispenser, thereby covering the membrane rupturing zone defined between the assemblies 26a and 26b so as to bind any broken membrane fragments and prevent same from being released into the animal or human. The polymeric film 50 also protects the device and improves the bio-compatibility thereof.

Figure 5:
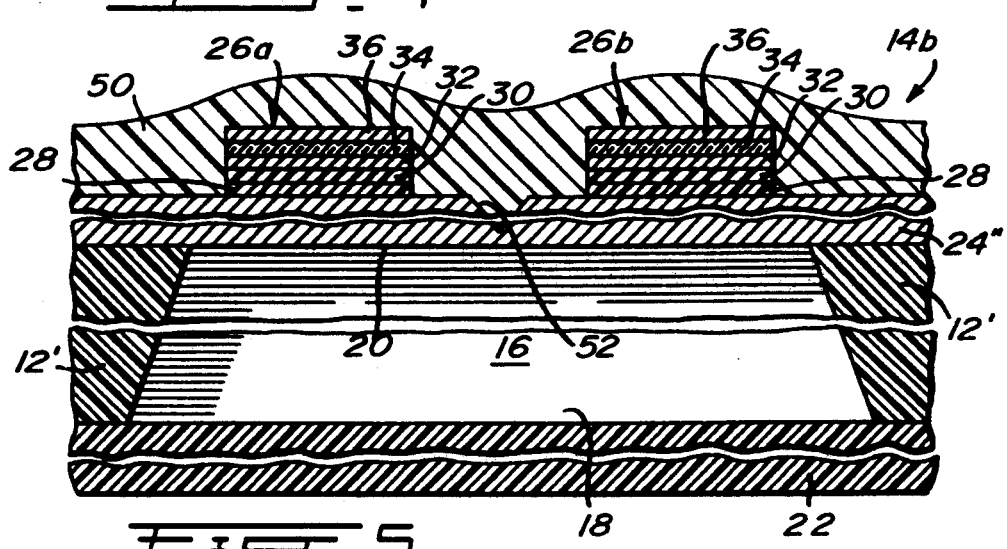
FIG. 5 is a view similar to FIG. 4, showing a medication delivery unit according to a yet further preferred embodiment of the invention.

Generally, the thin film 28, 30, 32, 34 and 36 have a thickness of about 0.5 μ. The thickness of the membrane 24 or 24' is typically about 10 μ. The body 12 or 12' and the closure member 22 may have a thickness of about 500 μ and 200 μ, respectively. If a membrane having a thickness greater than about 10 μ is utilized, such as in the case of the embodiment 14b illustrated in FIG. 5, a V-shaped groove 52 is advantageously formed in the membrane 24" between the assemblies 26a and 26b to define a line of weakness and thereby assist rupture of the membrane.

Figure 6:
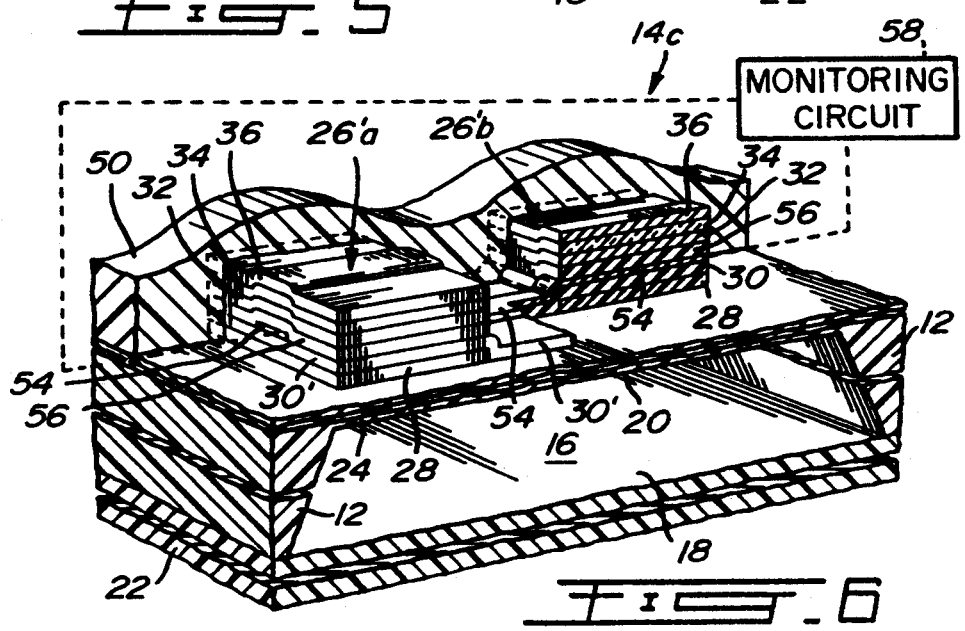
FIG. 6 is a view similar to FIG. 3, showing a medication delivery unit according to a still further preferred embodiment of the invention.

The medication delivery unit 14c illustrated in FIG. 6 features a detector system for detecting rupture of the membrane 24. The assemblies 26'a and 26'b of stacked thin films are similar to the assemblies 26a, 26b described above, except that a common electrically insulating thin film 30' is disposed on the stress-inducing thin film 28 of each assembly and extends on the membrane 24 over the membrane rupturing zone defined between the assemblies 26'a and 26'b. In addition, an electrically conductive thin film strip 54 is disposed on the thin film 30' to form an electrical path across the membrane rupturing zone, and a further electrically insulating thin film 56 is disposed over the thin film strip 54 of each assembly and between the thin films 30' and 32 thereof. The thin film strip 54 is connected by thin film leads (not shown) to a monitoring circuit 58 which detects the passage of electrical current through the thin film strip 54. Thus, rupture of the membrane 24 causes rupture of the thin film 30' and of the thin film strip 54 thereon so that the rupture of the membrane is detected by the monitoring circuit 58 as an open circuit. Intactness of the membrane 24, on the other hand, is detected as a closed circuit.

The monitoring circuit 58 can be integrated with the switching circuit 40. If, pursuant to the application of an electrical signal by the switching circuit 40 to the transducer 32,34,36 of assemblies 26'a and 26'b, the passage of electrical current in the thin film strip 54 is detected by the monitoring circuit 58, the membrane 24 is presumed to not have ruptured on command and the membrane rupturing system of an alternate medication delivery unit 14c is activated.

Figure 7:
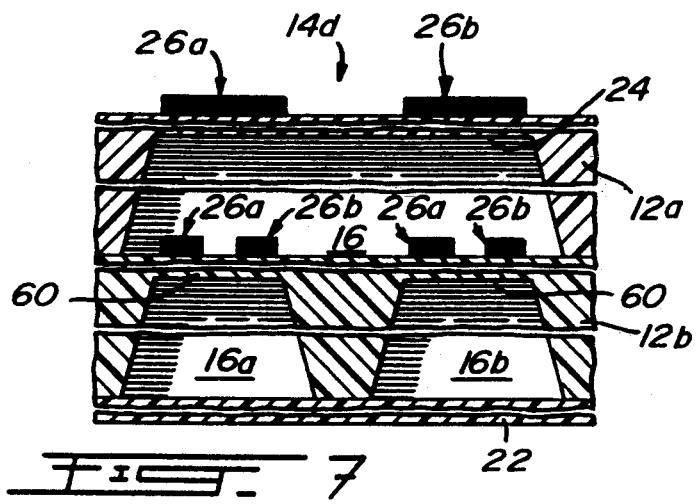
FIG. 7 is a fragmentary sectional view showing another type of medication delivery unit according to the invention.

Turning to FIG. 7, there is illustrated a medication delivery unit 14d especially adapted for the mixing of medicines prior to the delivery thereof into the animal or human body. As shown, the compartment 16 formed in the body portion 12a has two associated secondary compartments 16a and 16b formed in the body portion 12b and each containing a dose of different medicine to be mixed with the medicine contained in the compartment 16. The secondary compartments 16a and 16b are each separated from the compartment 16 by a partition comprising a rupturable silicon membrane 60 which is identical to the membrane 24 and anodically bonded to the body portion 12a. Each secondary compartment is provided with a membrane rupturing system 26a,26b for rupturing the membrane 60 thereof. The switching circuit 40 is operative to sequentially apply a first electrical signal to the membrane rupturing system 26a,26b of compartment 16a for causing rupture of the membrane 60 thereof and mixing of the medicines contained in compartments 16 and 16a, then a second electrical signal to the membrane rupturing system 26a,26b of compartment 16b for causing rupture of the membrane 60 thereof and mixing of the medicines contained in compartments 16 and 16b, and thereafter a third electrical signal to the membrane rupturing system 26a,26b of compartment 16 for causing rupture of the membrane 24 thereof and release of the mixed medicines into the animal or human body. If a slow mixing of the medicines is desired, an osmotic membrane can be used instead of membrane 60.

Figure 8:
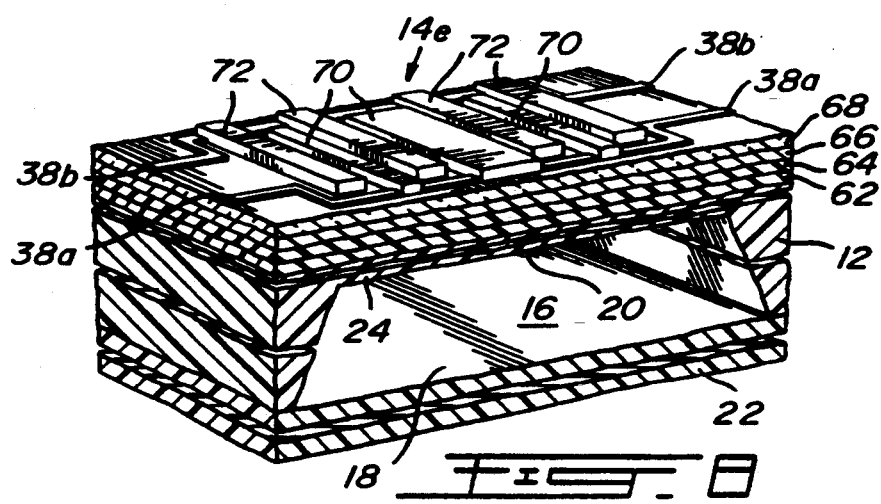
FIG. 8 is a fragmentary perspective view showing a still further type of medication delivery unit according to the invention.

FIG. 8 illustrates another type of medication delivery unit 14e which may be used in accordance with the invention. The membrane rupturing system of such a unit 14e, instead of being in the form of two spaced-apart assemblies of stacked thin films as described above, comprises a stress-inducing thin film 62 deposited on the membrane 24 and extending substantially completely over the delivery opening 20, an electrically insulating thin film 64 deposited on the thin film 62, an electrically conductive thin film 66 deposited on the thin film 64 and defining a ground electrode, a piezoelectric thin film 68 deposited on the thin film 66 and two electrically conductive thin films deposited on the thin film 68 and patterned to form a plurality of elongated voltage electrode elements 70,72 arranged in spaced-apart parallel relationship across the delivery opening 20 with the electrode elements 70 extending between the electrode elements 72. The stress-inducing thin film 62 is a thin film of polysilicon having properties similar to the stress-inducing thin film 28 previously described. The voltage electrode elements 70,72 extend in a common plane and are connected by the thin film leads 38a,38b to the switching circuit 40 shown in FIG. 1. The ground electrode 66 is similarly connected to the switching circuit 40 by a thin film lead (not shown).

The piezoelectric thin film 68 together with the ground electrode 66 and the voltage electrode elements 70,72 define a transducer which is responsive to the electrical signal supplied by the switching circuit 40, for applying to the membrane 24 the additional stress required to rupture same. By applying a positive voltage to the electrode elements 70 and a negative voltage to the electrode elements 72, the transducer will cause portions of the membrane 24 to undergo deformation in a common direction away from the compartment 16 so that the resulting stress in the membrane 24 will exceed the rupture point of the membrane, thereby causing rupture of same. Since the thin films 62,64,66,68 and electrode elements 70,72 each have a thickness of about 0.5 μ, rupture of the membrane 24 will lead to rupture of the overlying thin films and electrode elements.

The voltage electrode elements 70,72 are also connected to a monitoring circuit similarly as in FIG. 6, for detecting rupture of the membrane 24, of the thin films 62, 64,66, 68 and of the electrode elements 70, 72. Since rupture of the membrane 24 leads to rupture of the overlying thin films and electrode elements, such a rupture is detected by the monitoring circuit as an open circuit.

We claim:

1. A medication dispensing device for implantation into an animal or human body, said device comprising:
   a plurality of compartments each containing a dose of medicine to be dispensed and having a delivery opening permitting delivery of said medicine;
   a rupturable membrane sealing the delivery opening of each compartment, said membrane having a predetermined elastic deformation limit and a predetermined rupture point;

a plurality of membrane rupturing systems each associated with a respective one of said compartments and attached to the membrane thereof for rupturing same in response to an electrical signal, each said membrane rupturing system including stress-inducing means maintaining said membrane stressed to substantially the elastic deformation limit thereof, and piezoelectric transducer means responsive to said electrical signal for applying to said membrane additional stress sufficient to exceed the rupture point of said membrane and thereby cause rupture thereof, whereby to allow body fluids to enter into the compartment for mixing with the medicine contained therein so that said medicine is released in admixture with said body fluids through said delivery opening into the animal or human body; and means for supplying said electrical signal to a respective piezoelectric transducer means of each said membrane rupturing system to activate said respective piezoelectric transducer means.

2. The device of claim 1, wherein said device has a wafer-like body with a plurality of spaced-apart cavities formed therein, each cavity defining a respective one of said compartments.

3. The device of claim 2, wherein said membrane is integral with said wafer-like body.

4. The device of claim 2, wherein said cavities each extend through said wafer-like body to define a charging opening opposite said delivery opening for charging each compartment with said medicine, and wherein a closure member is bonded to said wafer-like body for sealing said charging openings.

5. The device of claim 1, wherein at least one of said compartments has at least one associated secondary compartment containing a dose of another medicine to be mixed with the medicine contained in said one compartment, said secondary compartment being separated from said one compartment by a partition comprising a further rupturable membrane, and wherein a further membrane rupturing system is associated with said secondary compartment for rupturing said further membrane thereof in response to a further electrical signal, said electrical signal supplying means being operative to sequentially apply said further electrical signal to said further membrane rupturing system and said electrical signal to said membrane rupturing system of said one compartment, whereby to first cause rupture of said further membrane and mixing of said medicine with said other medicine, and then cause rupture of said membrane of said one compartment for release of the mixed medicines into the animal or human body.

6. The device of claim 1, wherein said membrane has a line of weakness formed therein to assist rupturing same.

7. The device of claim 1, wherein each said membrane rupturing system comprises two assemblies of said stress-inducing means and said piezoelectric transducer means, said assemblies being arranged in spaced-apart opposed relationship on the membrane of each compartment, said stress-inducing means comprising a stress-inducing thin film on said membrane and said piezoelectric transducer means comprising two electrically conductive thin films and a piezoelectric thin film disposed therebetween, one of said electrically conductive thin films being arranged between said stress-inducing thin film and said piezoelectric thin film, and wherein said piezoelectric transducer means of said assemblies coact to apply to said membrane said additional stress and thereby cause said membrane to rupture between said assemblies.

8. The device of claim 7, wherein the piezoelectric transducer means of one assembly is operative to deform a portion of said membrane in a first direction and the piezoelectric transducer means of the other assembly is operative to deform an adjacent portion of said membrane in a second direction opposite said first direction, whereby to apply said additional stress to said membrane.

9. The device of claim 8, wherein said one electrically conductive thin film defines a ground electrode and the other electrically conductive thin film defines a voltage electrode, and wherein the electrical signal applied to said piezoelectric transducer means is such that the voltage electrode of said one assembly is positive with respect to the ground electrode thereof and the voltage electrode of said other assembly is negative with respect to the ground electrode thereof.

10. The device of claim 7, wherein an electrically insulating thin film is disposed between said stress-inducing thin film and said one electrically conductive thin film of each said assembly.

11. The device of claim 10, wherein said membrane is composed of silicon and said stress-inducing thin film is a thin film of polysilicon.

12. The device of claim 11, wherein said piezoelectric thin film is a thin film of lead zirconate titanate.

13. The device of claim 7, further including detector means associated with each compartment for detecting rupture of the membrane thereof.

14. The device of claim 13, wherein a common electrically insulating thin film is disposed between said stress-inducing thin film and said one electrically conductive thin film of each said assembly, said common electrically insulating thin film extending on said membrane between said assemblies over a membrane rupturing zone, and wherein said detector means comprises an electrically conductive thin film strip disposed on said common electrically insulating thin film and forming an electrical path across said membrane rupturing zone, and a monitoring circuit connected to said electrically conductive thin film strip for detecting passage of electrical current therethrough, a further electrically insulating thin film being disposed between said electrically conductive thin film strip and said one electrically conductive thin film of each said assembly, whereby rupture of said membrane causes rupture of said common electrically insulating thin film and of said electrically conductive thin film strip thereon so that rupture of said membrane is detected by said monitoring circuit as an open circuit.

15. The device of claim 1, wherein said stress-inducing means comprises a stress-inducing thin film disposed on the membrane of each compartment and extending substantially completely over the delivery opening thereof, said piezoelectric transducer means comprising first and second electrically conductive thin films defining respectively first and second voltage electrodes, a third electrically conductive thin film defining a ground electrode and a piezoelectric thin film disposed between said ground electrode and said first and second voltage electrodes, said ground electrode being arranged between said stress-inducing thin film and said piezoelectric thin film, and wherein each of said first and second voltage electrodes is patterned to form a plurality of elongated electrode elements arranged in spaced-apart parallel relationship across said delivery opening with the electrode elements of said first voltage electrode extending between the electrode elements of said second voltage electrode; said first and second voltage electrodes, said ground electrode and said piezoelectric thin film cooperating together to apply to said membrane said additional stress and thereby cause said membrane to rupture, rupture of said membrane leading to rupture of said stress-inducing thin film, said first, second and third electrically conductive thin films and said piezoelectric thin film.

16. The device of claim 15, wherein said first and second voltage electrodes and said ground electrode cooperate with said piezoelectric thin film to deform portions of said membrane in a common direction, whereby to apply said additional stress to said membrane.

17. The device of claim 16, wherein the electrical signal applied to said piezoelectric transducer means is such that said first voltage electrode is positive with respect to said ground electrode and said second voltage electrode is negative with respect no said ground electrode.

18. The device of claim 15, wherein the electrode elements of said first and second voltage electrodes extend in a common plane.

19. The device of claim 15, wherein an electrically insulating thin film is disposed between said stress-inducing thin film and said third electrically conductive thin film.

20. The device of claim 19, wherein said membrane is composed of silicon and said stress-inducing thin film is a thin film of polysilicon.

21. The device of claim 20, wherein said piezoelectric thin film is a thin film of lead zirconate titanate.

22. The device of claim 15, further including detector means associated with each compartment for detecting rupture of said membrane, said stress-inducing thin film, said first, second and third electrically conductive thin films and said piezoelectric thin film.

23. The device of claim 22, wherein said detector means comprises a monitoring circuit connected to a respective one of said first and second voltage electrodes for detecting passage of electrical current through the respective voltage electrode, whereby rupture of said membrane, said stress-inducing thin film, said first, second and third electrically conductive thin films and said piezoelectric thin film is detected by said monitoring circuit as an open circuit.

24. The device of claim 1, wherein said electrical signal supplying means comprises a power source and a time-controlled switching circuit for temporarily coupling said power source to said respective piezoelectric transducer means at a predetermined time.

25. The device of claim 1, further including a biocompatible polymeric film encapsulating said device.

* * * * *